(12) United States Patent
Badie et al.

(10) Patent No.: US 10,582,874 B2
(45) Date of Patent: Mar. 10, 2020

(54) METHOD AND DEVICE FOR ELECTROGRAM BASED ESTIMATION OF QRS DURATION

(71) Applicant: PACESETTER, INC., Sylmar, CA (US)

(72) Inventors: Nima Badie, Berkeley, CA (US); Jan Mangual-Soto, Rho (IT); Luke McSpadden, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 211 days.

(21) Appl. No.: 15/851,342

(22) Filed: Dec. 21, 2017

(65) Prior Publication Data
US 2019/0192028 A1    Jun. 27, 2019

(51) Int. Cl.
*A61B 5/04*       (2006.01)
*A61B 5/0472*     (2006.01)
*A61B 5/07*       (2006.01)
*A61B 5/0402*     (2006.01)
*A61B 5/042*      (2006.01)
(Continued)

(52) U.S. Cl.
CPC ........ *A61B 5/0472* (2013.01); *A61B 5/04004* (2013.01); *A61B 5/076* (2013.01); *A61B 5/04012* (2013.01); *A61B 5/04021* (2013.01); *A61B 5/0422* (2013.01); *A61B 5/0456* (2013.01); *A61B 5/6867* (2013.01)

(58) Field of Classification Search
CPC ............ A61B 5/04004; A61B 5/04012; A61B 5/04021; A61B 5/0422; A61B 5/0456; A61B 5/0472; A61B 5/076; A61B 5/6867
See application file for complete search history.

(56) References Cited

U.S. PATENT DOCUMENTS 6,751,504 B2   6/2004 Fishler
2006/0116596 A1   6/2006 Zhou et al.
(Continued)

OTHER PUBLICATIONS

Extended EP Search Report dated May 15, 2019—Counterpart EP Pat. App. 18214092.1.
(Continued)

*Primary Examiner* — George Manuel
(74) *Attorney, Agent, or Firm* — Dean D. Small; The Small Patent Law, Group, LLC

(57) ABSTRACT

Methods and devices are provided comprising an implantable lead having electrodes configured to be located proximate to a heart, the electrodes defining a sensing vector through a region of interest in the heart. The method and system collect an intra-cardiac electrogram (EGM) signal associated with an event of interest and determining an global amplitude characteristic (GAC) and a global slope characteristic (GSC) from the EGM signal under control of one or more processors within an implantable medical device (IMD). A QRS start time is defined, within the EGM signal, based on the GSC and determining a local amplitude characteristic (LAC) for a segment of the EGM signal within a search window of the GAC under control of one or more processors within an implantable medical device (IMD) A QRS end time is defined, within the EGM signal, based on the LAC; and calculating a QRS duration based on the QRS start time and QRS end time under control of one or more processors within an implantable medical device (IMD).

22 Claims, 8 Drawing Sheets

(51) Int. Cl.
*A61B 5/00* (2006.01)
*A61B 5/0456* (2006.01)

(56) References Cited

U.S. PATENT DOCUMENTS

| | | | |
|---|---|---|---|
| 2006/0206158 A1* | 9/2006 | Wu | A61N 1/36114 607/17 |
| 2008/0208069 A1* | 8/2008 | John | A61B 5/04012 600/509 |
| 2012/0310101 A1 | 12/2012 | Patangay et al. | |
| 2016/0045738 A1 | 2/2016 | Ghosh et al. | |
| 2016/0051821 A1 | 2/2016 | Sambelashvili et al. | |

OTHER PUBLICATIONS

Bachler, Martin et al., "Online and Offline Determination of QT and PR Interval and QRS Duration in Electrocardiography," ICPCA-SWS 2012, LNCS 7719, pp. 1-15.

\* cited by examiner

METHOD AND DEVICE FOR ELECTROGRAM BASED ESTIMATION OF QRS DURATION

BACKGROUND

Embodiments of the present disclosure generally relate to methods and devices for estimating a duration of a QRS complex based on intracardiac electrograms signals.

Implantable medical device programmable cardiac resynchronization therapy (CRT) based on various parameters. Changes in the CRT parameters have been shown to have an impact on clinical outcomes. Nonlimiting examples of CRT parameters include atrioventricular and interventricular activation delays (AVD and VVD, respectively), electrode configuration, and selection of paced ventricular chambers. Identifying a desired set of CRT parameters relies on an accurate assessment of relative cardiac function. Echocardiography and invasive left ventricular (LV) pressure measurements have been considered the gold standard for direct, comprehensive hemodynamic optimization of CRT parameters. However, echocardiography and LV pressure measurements are costly, time consuming, and must occur in a clinical environment.

Separately, surface electrocardiogram (ECG) signals have been utilized as a simpler alternative for assessing relative cardiac function. ECG signals may be utilized to determine whether electrical synchrony has been restored by CRT. More specifically, an ECG signal may be analyzed for a broad or narrow QRS complex. Dyssynchrony is typically associated with a broad QRS complex, while synchrony is typically associated with a narrow QRS complex.

However, the cardiovascular status of an individual patient constantly changes. Accordingly, continuous evaluation of, and adaptation to, the current cardiovascular status is necessary in order to maintain an optimal CRT parameter set. The use of surface ECG electrodes to collect ECG sisals represents a cumbersome, time-consuming and difficult system to provide continuous, ambulatory monitoring of the cardiac response to CRT.

SUMMARY

In accordance with an embodiment, a method is provided, comprising collecting an intra-cardiac electrogram (EGM) signal associated with an event of interest and determining an global amplitude characteristic (GAC) and a global slope characteristic (GSC) from the EGM signal under control of one or more processors within an implantable medical device (IMD). The method comprises defining a QRS start time, within the EGM signal, based on the GSC and determining a local amplitude characteristic (LAC) for a segment of the EGM signal within a search window of the GAC under control of one or more processors within an implantable medical device (IMD). The method further comprises defining a QRS end time, within the EGM signal, based on the LAC, and calculating a QRS duration based on the QRS start time and QRS end time under control of one or more processors within an implantable medical device (IMD).

Optionally, the GAC may represent a global amplitude minimum experienced by the EGM signal over the event of interest. The GSC may represent a global slope minimum experienced by the EGM signal over the event of interest. The defining the QRS start time further may comprise defining the QRS start time as a last time point along the QRS complex before a point in time at which the GSC exhibited at least one of: a derivative of the EGM signal exceeds the global slope characteristic by a predetermined slope factor or the EGM signal exceeds the global amplitude minimum by a predetermined amplitude factor.

Optionally the determining the GSC may include calculating derivatives at points along the EGM signal over a search window that precedes the GAC and determining the global slope minimum in a negative direction based on the derivatives. The method may further comprise reducing the QRS start time by an amount corresponding to an isoelectric drop.

Optionally, the determining the LAC may comprise determining a local amplitude maximum that occurs within a search window after the GAC; and identifying threshold crossings of the EGM signal that surround the local amplitude maximum, the threshold crossings representing points at which the EGM signal cross a threshold amplitude that is defined based on the local amplitude maximum. The QRS end time may be determined to correspond to a point in time along the EGM signal at a set point between the threshold crossings.

Optionally, the method may, further comprise determining whether a deflection spike occurs prior to the QRS start time, verifying whether the deflection spike represents a local maximum amplitude, and adjusting the QRS start time based on the verifying to a point in time before the deflection spike. The method may also comprising determining whether a deflection spike occurs prior to the QRS start time, verifying whether a slope of the EGM signal within a search window prior to the deflection spike falls below the global slope characteristic by a slope factor, and adjusting the QRS start time based on the verifying to a point in time before the deflection spike.

In accordance with an embodiment, a system is provided comprising an implantable lead having electrodes configured to be located proximate to a heart, the electrodes defining a sensing vector through a region of interest in the heart. The system includes memory to store program instructions; and a processor. The processor, when executing the program instructions, is configured to collect an intra-cardiac electrogram (EGM) signal along the sensing vector, the EGM signal associated with an event of interest; determine an global amplitude characteristic (GAC) and a global slope characteristic (GSC) from the EGM signal. The processor is further configured to define a QRS start time, within the EGM signal, based on the GSC; determine a local amplitude characteristic (LAC) for a segment of the EGM signal within a search window of the GAC, define a QRS end time, within the EGM signal, based on the LAC, and calculate a QRS duration based on the QRS start and QRS end.

Optionally, the GAC may represent a global amplitude minimum experienced by the EGM signal over the event of interest. The GSC may represent a global slope minimum experienced by the EGM signal over the event of interest.

Optionally, the processor may be configured to define the QRS start time as a last time point along the QRS complex before a point in time at which the GSC exhibited at least one of: I) a slope of the EGM signal exceeds the global slope minimum by a predetermined slope factor or II) the EGM signal exceeds the global amplitude minimum by a predetermined amplitude factor. The processor may also be configured to calculate derivatives at points along the EGM signal over a search window that precedes the GAC and to determine the global slope minimum in a negative direction based on the derivatives.

Optionally, the system may further comprise reducing the QRS start time by an amount corresponding to an isoelectric drop. The determining the LAC may comprise determining a local amplitude maximum that occurs within a time window after the GAC; and identifying threshold crossings of the EGM signal that surround the local amplitude maximum, the threshold crossings representing points at which the EGM signal cross a threshold amplitude that is defined based on the local amplitude maximum. The QRS end time may be determined to correspond to a point in time along the EGM signal at a set point between the threshold crossings.

Optionally, the processor may further be configured to determine whether a deflection spike occurs prior to the QRS start time, verifying whether the deflection spike represents a local maximum amplitude, and adjusting the QRS start time based on the verifying to a point in time before the deflection spike. The processor may further be configured to determine whether a deflection spike occurs prior to the QRS start time, verifying whether a slope of the EGM signal within a time window prior to the deflection spike falls below the global slope characteristic by a slope factor, and, based on the verifying, adjusting the QRS start time to a point in time before the deflection spike.

DETAILED DESCRIPTION

Figure 1:
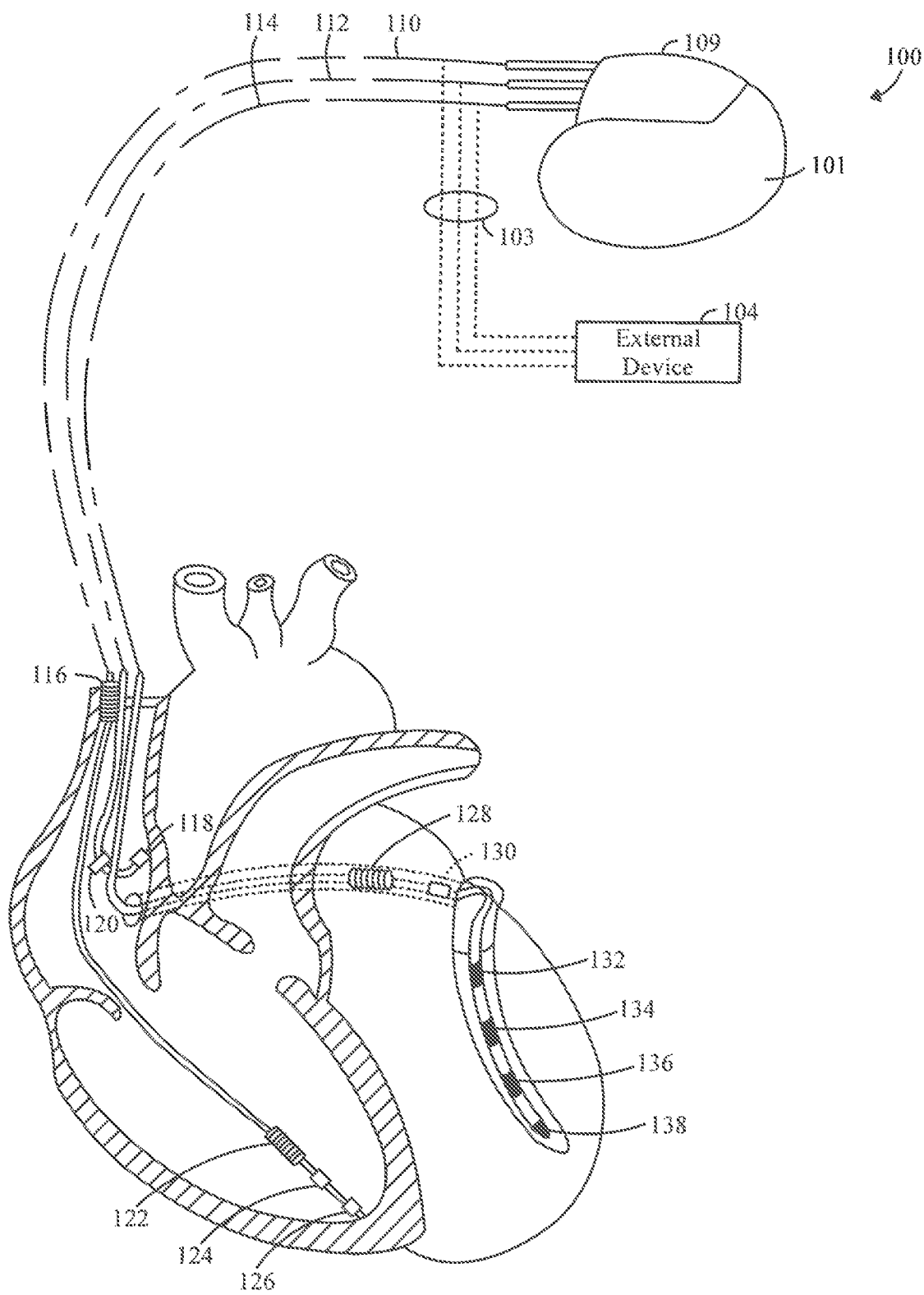
FIG. 1 illustrates an implantable medical device and external device coupled to a heart in a patient and implemented in accordance with one embodiment.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless implantable Medical Device Having Removable And Fixed Components" and U.S. Pat. No. 8,831,747 "Leadless Neurostimulation Device And Method including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical. Device" and U.S. Pat. No. 9,232,485 "System And Method For Selectively Communicating With An Implantable Medical Device", which are hereby incorporated by reference.

The terms "minimum", "maximum", "optimal" and similar terminology, as used herein, do not necessarily refer to a particular point or numeric value, but instead may refer to a range having a variation that would be expected to have limited impact on a physiologic result. By way of example, an amplitude, slope or other characteristic of an EGM signal may vary within a range (e.g., +/−5%), while still being considered a minimum, maximum, or optimal value.

The terms "minimum" and "maximum" are without regard for positive or negative values, and more generally may be used to refer to absolute values of an EGM signal. For example, a minimum may be a minimum "negative" or a minimum "positive" value. Similarly, a maximum may be a maximum "negative" or a maximum "positive" value.

The term "global" is used throughout to refer to a characteristic of an EGM signal for a complete cardiac cycle or heartbeat. For example, a global amplitude maximum, would represent a maximum amplitude exhibited over the EGM signal for a complete cardiac cycle. As another example, a global slope maximum, would represent a maximum slope exhibited over the EGM signal for a complete cardiac cycle.

The term "local" is used throughout to refer to a characteristic of a segment of an EGM signal for a subsection or phase of a cardiac cycle or heartbeat. For example, a local amplitude maximum, would represent a maximum amplitude exhibited over a segment within the EGM signal for a part of a cardiac cycle (e.g., within a search window having a duration of a few milliseconds). As another example a local slope maximum, would represent a maximum slope exhibited over a segment within the EGM signal for a part of a cardiac cycle. The EGM signal for one cardiac cycle may be divided into multiple segments, each of which exhibits a local amplitude maximum and a local slope maximum within the different corresponding search windows.

Embodiments herein provide a closed-loop, implantable device-based alternative to surface ECG based systems, where the implantable device-based solution is not limited to in-clinic measurements (e.g., surface ECG). Embodiments herein provide implantable device-based methods and devices to estimate QRS duration solely based on intracardiac electrograms (EGMs). The QRS duration estimation may be implemented as part of an IMD and medical platforms, such as an automated synchronous atrial and ventricular CRT programming and optimization workflow.

FIG. 1 illustrates an IMD 100 and external device 104 coupled to a heart in a patient and implemented in accordance with one embodiment. The external device 104 may be a programmer, an external defibrillator, a workstation, a portable computer, a personal digital assistant, a cell phone, a bedside monitor and the like. The IMD 100 may represent a cardiac monitoring device, pacemaker, cardioverter, cardiac rhythm management device, defibrillator, neurostimulator, leadless monitoring device, leadless pacemaker and the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 100 are discussed and illustrated in the drawings herewith.

The IMD 100 includes a housing 101 that is joined to a header assembly 109 that holds receptacle connectors connected to a right ventricular lead 110, a right atrial lead 112, and a coronary sinus lead 114, respectively. The leads 112, 114 and 110 measure cardiac signals of the heart. The right atrial lead 112 includes an atrial tip electrode 118 and an atrial ring electrode 120. The coronary sinus lead 114 includes a left atrial ring electrode 128, a left atrial coil electrode 130 and one or more left ventricular electrodes 132-138 (e.g., also referred to as P1, M1, M2 and D1) to form a multi-pole LV electrode combination. The right ventricular lead 110 includes an RV tip electrode 126, an RV ring electrode 124, an RV coil electrode 122, and an SVC coil electrode 116. The leads 112, 114 and 110 detect EGM signals that are processed and analyzed as described herein. The leads 112, 114 and 110 also delivery therapies as described herein.

During implantation, the external device 104 is connected to one or more of the leads 112, 114 and 110 through temporary inputs 103. The inputs 103 of the external device 104 receive EGM signals from the leads 112, 114 and 110 during implantation and display the EGM signals to the physician on a display. Optionally, the external device 104 may not be directly connected to the leads 112, 114 and 110. Instead, the EGM cardiac signals sensed by the leads 112, 114 and 110 may be collected by the IMD 100 and then transmitted wirelessly to the external device 104. Hence, the external device 104 receives the EGM cardiac signals through telemetry circuit inputs. The physician or another user controls operation of the external device 104 through a user interface.

Implantable Medical Device

Figure 2:
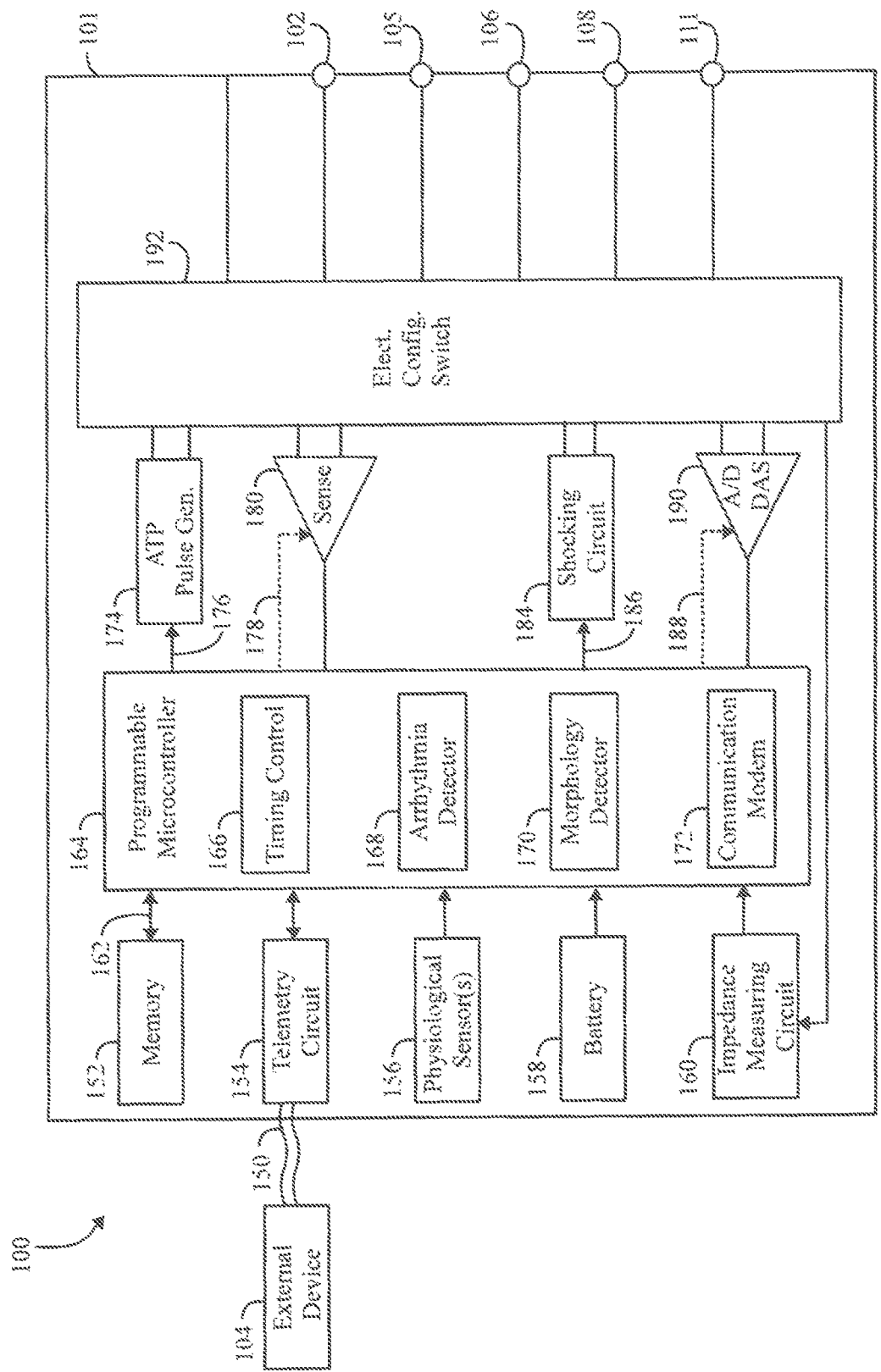
FIG. 2 shows an exemplary IMD 100 that is implanted into the patient as part of the implantable cardiac system in accordance with embodiments herein.

FIG. 2 shows an exemplary IMD 100 that is implanted into the patient as part of the implantable cardiac system. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing.

The IMD 100 has a housing 101 to hold the electronic/computing components. The housing 101 (which is often referred to as the "can", "case", "encasing", or "case electrode") may be programmably selected to act as the return electrode for certain stimulus modes. The housing 101 further includes a connector (not shown) with a plurality of terminals 102, 105, 106, 108, and 111. The terminals may be connected to electrodes that are located in various locations within and about the heart. For example, the terminals may include: a terminal 102 to be coupled to an first electrode (e.g., a tip electrode) located in a first chamber; a terminal 105 to be coupled to a second electrode (e.g., tip electrode) located in a second chamber; a terminal 106 to be coupled to an electrode (e.g., ring) located in the first chamber; a terminal 108 to be coupled to an electrode located (e.g., ring electrode) in the second chamber; and a terminal 111 to be coupled to an electrode (e.g., coil) located in the SVC. The type and location of each electrode may vary. For example, the electrodes may include various combinations of ring, tip, coil and shocking electrodes and the like.

The IMD 100 includes a programmable microcontroller 164 that controls various operations of the IMD 100, including cardiac monitoring and stimulation therapy. The microcontroller 164 includes a microprocessor (or equivalent control circuitry), RAM and/or ROM memory, logic and timing circuitry, condition machine circuitry, and I/O circuitry.

IMD 100 further includes a first chamber pulse generator 174 that generates stimulation pulses for delivery by one or more electrodes coupled thereto. The pulse generator 174 is controlled by the microcontroller 164 via control signal 176. The pulse generator 174 is coupled to the select electrode(s) via an electrode configuration switch 192, which includes multiple switches for connecting the desired electrodes to the appropriate I/O circuits, thereby facilitating electrode programmability. The switch 192 is controlled by a control signal 186 from the microcontroller 164.

In the example of FIG. 1, a single pulse generator 174 is illustrated. Optionally, the IMD 100 may include multiple pulse generators, similar to pulse generator 174, where each pulse generator is coupled to one or more electrodes and controlled by the microcontroller 164 to deliver select stimulus pulse(s) to the corresponding one or more electrodes.

Microcontroller 164 is illustrated to include timing control circuitry 166 to control the timing of the stimulation pulses for CRT (e.g., pacing rate, atrio-ventricular (AV) delay, atrial interconduction (A-A) delay, or ventricular interconduction (V-V) delay, etc.). The timing control circuitry 166 may also be used for the timing of search windows, refractory periods, blanking intervals, noise detection windows, evoked response windows, alert intervals, marker channel timing, and so on. Microcontroller 164 also has an arrhythmia detector 168 for detecting arrhythmia conditions and a morphology detector 170 to review and analyze one or more features of the morphology of cardiac signals. Although not shown, the microcontroller 164 may further include other dedicated circuitry and/or firmware/software components that assist in monitoring various conditions of the patient's heart and managing pacing therapies.

The IMD 100 is further equipped with a communication modem (modulator/demodulator) 172 to enable wireless communication with other devices, implanted devices and/or external devices. In one implementation, the communication modem 172 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The communication modem 172 may be implemented in hardware as part of the microcontroller 164, or as software/firmware instructions programmed into and executed by the microcontroller 164. Alternatively, the communication modem 172 may reside separately from the microcontroller as a standalone component.

The IMD 100 includes sensing circuitry 180 selectively coupled to one or more electrodes that perform sensing operations, through the switch 192 to detect the presence of EGS signals along various sensing vectors. The sensing circuitry 180 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics (e.g., atrial fibrillation). Switch 192 determines the sensing polarity of the cardiac signal by selectively closing the appropriate switches. In this way, the clinician may program the sensing polarity independent of the stimulation polarity.

The output of the sensing circuitry 180 is connected to the microcontroller 164 which, in turn, triggers or inhibits the pulse generator 174 in response to the absence or presence of certain types of cardiac activity. The sensing circuitry 180 receives a control signal 178 from the microcontroller 164 for purposes of controlling the gain, threshold, polarization charge removal circuitry (not shown), and the timing of any blocking circuitry (not shown) coupled to the inputs of the sensing circuitry.

In the example of FIG. 1, a single sensing circuit 180 is illustrated. Optionally, the IMD 100 may include multiple sensing circuit, similar to sensing circuit 180, where each sensing circuit is coupled to one or more electrodes and controlled by the microcontroller 164 to sense electrical activity as EGM signals detected at the corresponding one or more electrodes. The sensing circuit 180 may operate in a unipolar sensing configuration or in a bipolar sensing configuration.

The IMD 100 further includes an analog-to-digital (A/D) data acquisition system (DAS) 190 coupled to one or more electrodes via the switch 192 to sample cardiac signals across any pair of desired electrodes. The data acquisition system 190 is configured to acquire intracardiac electrogram signals, convert the raw analog data into digital data, and store the digital data for later processing and/or telemetric transmission to an external device 104 (e.g., a programmer, local transceiver, or a diagnostic system analyzer). The data acquisition system 190 is controlled by a control signal 188 tip the microcontroller 164.

Figure 3A:
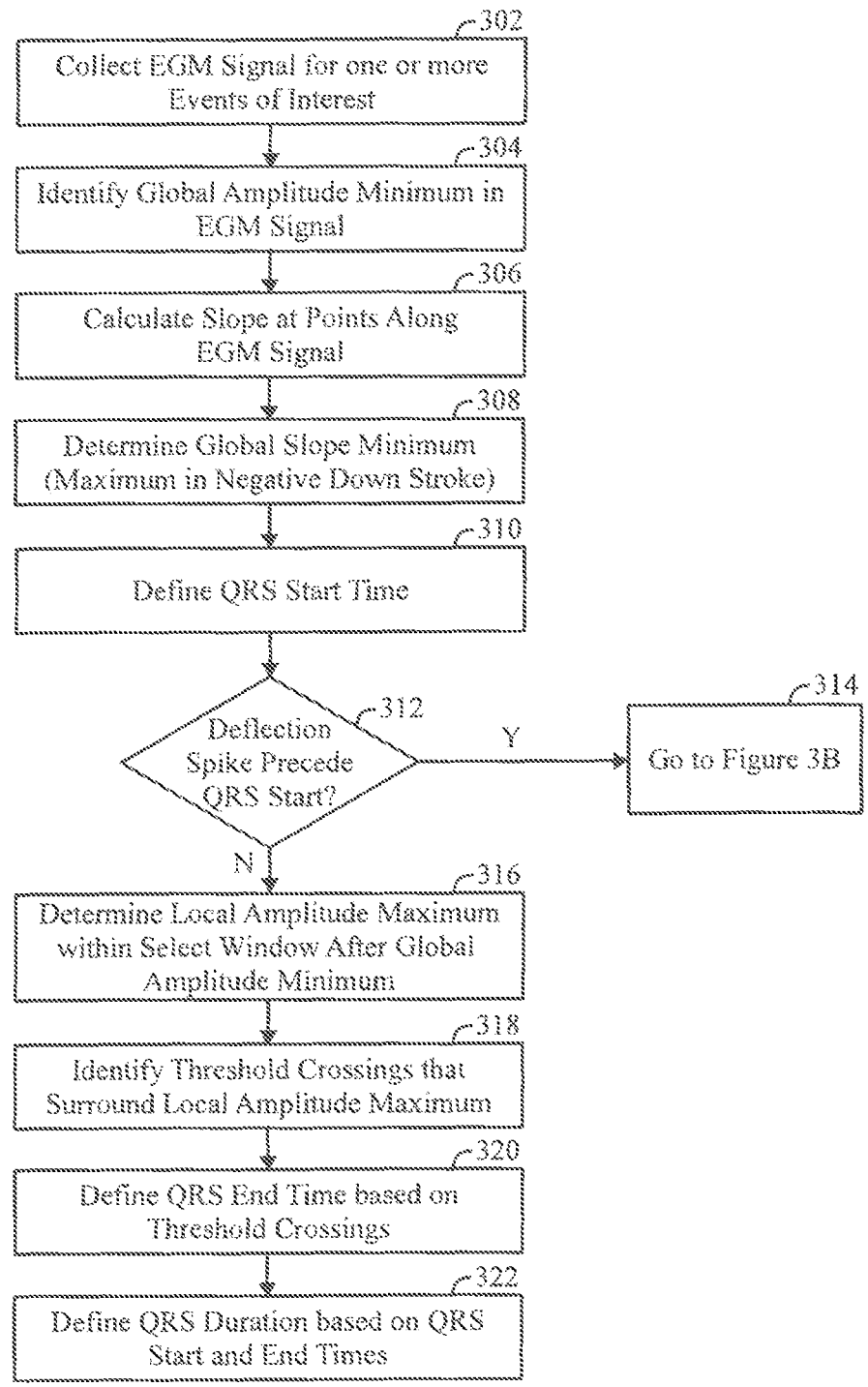
FIGS. 3A and 3B illustrate a process for estimating a duration of a QRS complex from intracardiac electrograms in accordance with embodiments herein.

In connection with FIG. 3A, an EGM signal is sensed along a far field sensing vector that may be defined between various combinations of electrodes located within or proximate to the heart. For example, the sensing vector may be between an RV coil electrode and a can/housing of an IMD. Additionally or alternatively, the sensing vector may be defined between electrode combinations that are spaced with a desired portion, or a majority of the heart between the electrodes. For example, the sensing vector may be between the RV coil and an LV electrode. Optionally, the sensing vector may be between another RV electrode (e.g., tip or ring) and a can/housing of the IMD and/or an LV electrode. The electrodes may be configured to have a particular anode/cathode combination. For example, the RV coil electrode may be defined as the anode, while the can/housing of the IMD is defined as the cathode.

The microcontroller 164 is coupled to a memory 152 by a suitable data/address bus 162. The programmable operating parameters used by the microcontroller 164 are stored in memory 152 and used to customize the operation of the IMD 100 to suit the needs of a particular patient. Such operating parameters define, for example, CRT parameters, pacing pulse amplitude, pulse duration, electrode polarity, rate, sensitivity, automatic features, arrhythmia detection criteria.

The operating parameters of the IMD 100 may be non-invasively programmed into the memory 152 through a telemetry circuit 154 in telemetric communication via communication link 150 with the external device 104 (e.g., Bluetooth, low energy Bluetooth, or other wireless protocol). The telemetry circuit 154 allows intracardiac electrograms and status information relating to the operation of the IMD 100 (as contained in the microcontroller 164 or memory 152) to be sent to the external device 104 through the established communication link 150.

The IMD 100 can optionally include magnet detection circuitry (not shown), coupled to the microcontroller 164, to detect when a magnet is placed over the unit. A magnet may be used by a clinician to perform various test functions of the unit 100 and/or to signal the microcontroller 164 that the external programmer is in place to receive or transmit data to the microcontroller 164 through the telemetry circuits 154.

The IMD 100 can further include one or more physiologic sensors 156. Such sensors are commonly referred to as "rate-responsive" sensors because they are typically used to adjust pacing stimulation rates according to the exercise condition of the patient. However the physiological sensor 156 may further be used to detect changes in cardiac output, changes in the physiological condition of the heart, or diurnal changes in activity (e.g., detecting sleep and wake conditions). Signals generated by the physiological sensors 156 are passed to the microcontroller 164 for analysis. The microcontroller 164 responds by adjusting the various pacing parameters (such as rate, AV Delay, V-V Delay, etc.) at which the atrial and ventricular pacing pulses are administered. While shown as being included within the unit 100, the physiologic sensor(s) 156 may be external to the unit 100, yet still be implanted within or carried by the patient. Examples of physiologic sensors might include sensors that, for example, sense respiration rate, pH of blood, ventricular gradient, activity, position/posture, minute ventilation (MV), and so forth.

A battery 158 provides operating power to all of the components in the IMD 100. The battery 158 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the IMD 100 employs lithium/silver vanadium oxide batteries.

The IMD 100 further includes an impedance measuring circuit 160, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 160 is coupled to the switch 192 so that any desired electrode may be used.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 164 further controls a shocking circuit 184 by way of a control signal 186. The shocking circuit 184 generates shocking pulses of low (e.g., up to 0.5 joules), moderate (e.g., 0.540 joules), or high energy (e.g., 111 to 50 joules), as controlled by the microcontroller 164. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

The microcontroller 164 is configured to execute the program instructions to perform the operations described herein. The microcontroller 164 is configured to collect an EGM signal along one or more sensing vector, where the EGM signal is associated with an event of interest. The microcontroller 164 is configured to determine an global amplitude characteristic (GAC) and a global slope characteristic (GSC) from the EGM signal, to define a QRS start time, within the EGM signal, based on the GSC, and to determine a local amplitude characteristic (LAC) for a segment of the EGM signal within a search window of the GAC. The microcontroller 164 is configured to define a QRS end time, within the EGM signal, based on the LAC and calculate a QRS duration based on the QRS start and QRS end. The GAC may represent a global amplitude minimum experienced by the EGM signal over the event of interest, and the GSC may represent a global slope minimum experienced by the EGM signal over the event of interest. The microcontroller 164 may be further configured to define the QRS start time as a last time point along the QRS complex before a point in time at which the GSC exhibited at least one of: I) a slope of the EGM signal exceeds the global slope minimum by a predetermined slope factor or II) the EGM signal exceeds the global amplitude minimum by a predetermined amplitude factor. The microcontroller 164 may be further configured to calculate derivatives at points along the EGM signal over a search window that precedes the GAC and to determine the global slope minimum in a negative direction based on the derivatives. The microcontroller 164 is configured to reduce the QRS start time by an amount corresponding to an isoelectric drop. The determining of the LAC may comprise determining a local amplitude maximum that occurs within a time window after the GAC, and identifying threshold crossings of the EGM signal that surround the local amplitude maximum, where the threshold crossings represent points at which the EGM signal cross a threshold amplitude that is defined based on the local amplitude maximum.

Optionally, the microcontroller 164 determines the QRS end time to correspond to a point in time along the EGM signal at a set point between the threshold crossings. Optionally, the microcontroller 164 is further configured to determine whether a deflection spike occurs prior to the QRS start time, and based thereon, verify whether the deflection spike represents a local maximum amplitude. The microcontroller 164 adjusts the QRS start time based on the verifying to a point in time before the deflection spike. Optionally, the microcontroller 164 is further configured to determine whether a deflection spike occurs prior to the QRS start time, and based thereon, verify whether a slope of the EGM signal within a time window prior to the deflection spike falls below the global slope characteristic by a slope factor. Based on the verifying operation, the microcontroller 164 adjusts the QRS start time to a point in time before the deflection spike. The operations of the microcontroller 164 are described below in more detail.

QRS Duration Estimation

Figure 3B:
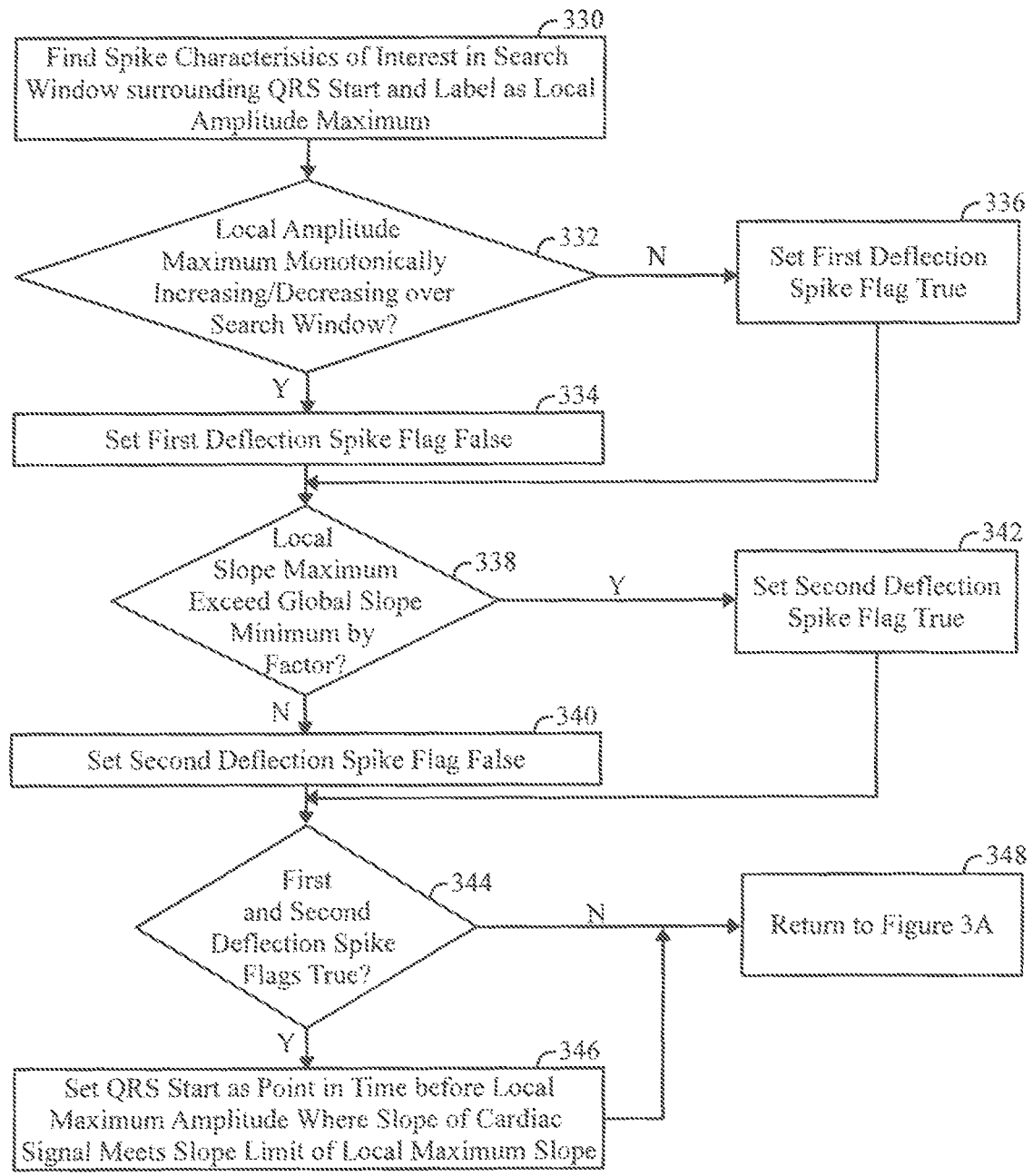

FIGS. 3A and 3B illustrate a process for estimating a duration of a QRS complex from intracardiac electrograms in accordance with embodiments herein. The operations of FIG. 3A are implemented by one or more processors of the devices and systems described herein, such as an IMD and/or an external device.

At 302, the one or more processors collect intracardiac electrograms (EGM) signals in connection with one or more events of interest. By way of example, the EGM signals may be collected by a leadless IMD, a lead-based IMD coupled to one or more leads and/or an external device coupled to one or more implanted leads. The one or more leads have electrodes configured to be implanted proximate to regions of interest (e.g., within and/or surrounding the heart). Electrode combinations may be selected to define sensing vectors of interest, where the sensing vectors (e.g., RV coil-to-can, RV coil-to-LV electrode) extend through regions of interest. For example, the sensing vector may be between an RV coil electrode and a can/housing of an IMD. Additionally or alternatively, the sensing vector may be defined between electrode combinations that are spaced with a desired portion, or a majority of, the heart between the electrodes. For example, the sensing vector may be between the RV coil and an LV electrode. Optionally, the sensing vector may be between another RV electrode (e.g., tip or ring) and a can/housing of the IMD and/or an LV electrode. The electrodes may be configured to have a particular anode/cathode combination. For example, the RV coil electrode may be defined as the anode, while the can/housing of the IMD is defined as the cathode. The EGM signals are representative of activity along the sensing vectors. The same or different electrodes may be utilized to deliver CRT therapy in accordance with CRT parameters.

The collection operation at 302 may be performed in connection with a single event of interest (e.g. one cardiac cycle or one beat). Additionally or alternatively, EGM signals may be collected for two or more events of interest. When EGM signals are collected for more than one event of interest, the EGM signals for each event/beat may be separately analyzed as described hereafter in connection with FIGS. 3A and 3B. Additionally or alternatively, the EGM signals for multiple events/beats may be combined, such as to form an EGM ensemble (e.g., average or other mathematical combination of multiple EGM signals).

At 304-310, the one or more processors analyze the EGM signal to define a QRS start time for a QRS complex. At 304, the one or more processors analyze an amplitude at multiple points along the EGM signal to determine a global amplitude characteristic (GAC) from the EGM signal. For example, the GAC may represent a global amplitude minimum experienced by the cardiac signal over the event of interest.

At 306 to 308, the one or more processors determine a global slope characteristic (GSC) from the EGM signal. For example, the GSC may represent a global slope maximum experienced by the EGM signal over the event of interest. At 306, the one or more processors calculate derivatives at points along the EGM signal over a desired search window that precedes the GAC. At 308, the one or more processors determine the negative global slope minimum from the derivatives along the EGM signal. For example, the global slope minimum may represent a maximum negative down stroke of the EGM signal.

At 310, the one or more processors define the QRS start time, within the EGM signal, based on the GSC. For example, as explained below in connection with FIGS. 4A and 4B, when the GSC represents a global slope minimum, the processors define the QRS start time as a last time point along the QRS complex before a point in time at which the GSC (e.g., global slope minimum) exhibited at least one of the following conditions: I) a derivative/slope of the EOM signal exceeds or is approximately equal to a predetermined slope factor of the global slope minimum and/or II) the EGM signal exceeds or is approximately equal to a predetermined amplitude factor of the global amplitude minimum. For example, one condition may be that a ratio of i) the dV/dt of the EGM signal V(t) and ii) the global slope minimum $dV/dt_{min}$ exceeds or is approximately equal to 5%. The other condition may be that a ratio of i) the EGM signal V(t) and ii) the global amplitude minimum $V_{min}$ exceeds or is approximately 10%. It is recognized that the foregoing slope and amplitude factors are examples and may vary.

Additionally or alternatively, the processors may define the QRS start time at the point in time at which the GSC exhibits both of the foregoing conditions (I) and (II). Optionally, the QRS start time may be adjusted by a predefined amount to account for are isoelectric drop. For example, the QRS start time may be reduced by 5 ms (or some other amount that is empirically defined) to account for the isoelectric drop.

At 312, the one or more processors determine whether to test for a potential deflection spike that may precede the QRS start time. When it is desirable to test for deflection spikes, flow branches to 314. For example, the determination at 312 may be based on a determination by the processors that the EGM signal exhibited a positive deflection or exceeded some baseline level before the global amplitude minimum determined at 304. As another option, the processors may base the decision at 312 on a determination that the EGM signal exhibited a local amplitude maximum within a window surrounding the QRS start time and/or before the global amplitude minimum.

At 314, the one or more processors test for a deflection spike and when present adjust the QRS start time. After 314, flow returns to 316. Optionally, the decision at 312 may be omitted and instead flow may move directly from 310 to 314. Optionally, the operations at 312 and 314 may be omitted entirely.

At 316, the one or more processors determine a local amplitude characteristic (LAC) for the EGM signal within a select local search window. The local amplitude characteristic may represent a local amplitude maximum exhibited by the EGM signal during the search window. The search window is positioned based on the GAC. For example, the search window may be set to a duration of 200 ms and may be aligned temporally to begin at or shortly after the GAC (e.g., global amplitude minimum). Optionally, a duration and start point of the search window may be varied.

At 318, the one or more processors identify two or more threshold crossings of the EGM signal. To do so, the processors define a threshold amplitude based on the local amplitude maximum. For example, the threshold amplitude may be defined to be a select percentage (e.g., 90%) of the LAC (e.g., local amplitude maximum). The processors identify at least first and second points where the EGM signal crosses the threshold amplitude, where the first and second points occur before and after the LAC. The first and second points are labeled as first and second threshold crossing points $t_1$ and $t_2$, and surround the local amplitude maximum.

At 320, the one or more processors define a QRS end time, within the EGM signal, based on the LAC. For example, the QRS endpoint is determined to correspond to a point in time along the EGM signal at a set distance between the first and second threshold crossing points $t_1$ and $t_2$. As a further example, the QRS endpoint may be set at a desired distance along the range between the first and second threshold crossing points $t_1$ and $t_2$, such as 80% along the range between the first and second threshold crossing points $t_1$ and $t_2$.

At 322, the one or more processors calculate a QRS duration based on the QRS start point and QRS end point. For example, the QRS duration may be set to equal the time duration between the QRS start and end points. Additionally or alternatively, the QRS duration may be defined as a percentage (e.g., 90%, 110%) of the duration between the QRS start and end points. The QRS duration is saved in memory, such as in the IMD, external device, remote server and the like. The QRS duration may then be used for various reasons such as to determine whether a CRT therapy is effective or ineffective at achieving synchronous physiologic behavior of the heart as explained below in connection with FIG. 3C.

Optionally, the operations of FIG. 3A may be performed periodically or upon demand from an external device, and/or based on indicators from the cardiac signals. For example, indications may be identified in connection with monitoring whether a CRT therapy is effective or ineffective. Optionally, the CRT therapy may be adjusted based on a single QRS duration estimate and/or based on multiple iterations through the operations of FIGS. 3A and 3B over a period of time.

FIG. 3B illustrates a process for validating deflection spikes in accordance with embodiments herein. As explained above, flow moves to FIG. 3B from 314 in FIG. 3A when it is desirable to determine whether the QRS start time is preceded by a deflection spike. Optionally, the operations of FIG. 3B may be performed at other points within, before, or after the operations of FIG. 3A. (e.g., after 320 but before 322).

At 330, the one or more processors define a search window located proximate to the QRS start time (determined at 310 in FIG. 3A). For example, the search window (also referred to as a deflection spike search window) may be positioned to surround the QRS start time by extending back in time a desired duration and forward in time a desired duration (e.g., starting 30 ms before the QRS start time and ending 10 ms after the QRS start time). Optionally, the search window may be varied in length and/or shifted to extend further back in time, or to extend a shorter distance back in time, preceding the QRS start time. The processors analyze the EGM signal segment within the search window for a characteristic of interest indicative of a deflection spike. The characteristic of interest may represent a local amplitude maximum $V_{max}^{spike}$, in which case the processors analyze the EGM signal in the search window to identify the local amplitude maximum.

At 332-342, the one or more processors analyze characteristics of the EGM signal segment that falls within the search window in order to validate or deny the deflection spike. The deflection spike is considered a "candidate" until validated or denied. By way of example, a characteristic of interest may relate to whether the EGM signal is monotonically increasing or decreasing over the search window. As another example, a characteristic of interest may relate to a slope of the EGM signal relative to the global slope minimum.

At 332, the one or more processors analyze the segment of the EGM signal, within the deflection spike search window, surrounding the local amplitude maximum. The processors find a local amplitude maximum $V_{max}^{spike}$ in the search window. The local amplitude maximum $V_{max}^{spike}$ represents a maximum of an absolute value of the EGM signal V(t) in the search window. The processors determine whether the EGM signal V(t) is monotonically increasing or decreasing from the local amplitude maximum $V_{max}^{spike}$ over all or a majority of the search window. When the segment of the EGM signal monotonically increases or decreases from the local amplitude maximum $V_{max}^{spike}$ over the search window, flow continues to 334. Otherwise, flow branches to 336. At 334, the one or more processors set a first deflection flag to a false condition indicating that the EGM signal segment is not monotonically changing. At 336, the one or more processors set the deflection flag to a true condition indicating that the EGM signal segment is monotonically changing. The analysis at 332 seeks to determine whether the local amplitude maximum is indeed a local maximum, or instead merely a peak (e.g., at a leading or trailing end of the search window) along a continuously increasing or decreasing segment of the EGM signal. To have a local amplitude maximum, the EGM signal would not monotonically increase or decrease across the search window. Accordingly, the one or more processors set a first deflection flag to a true or false condition based on the determination at 332.

At 338, the one or more processors analyze a pre-spike search window that precedes the local amplitude maximum $V_{max}^{spike}$ to identify a local slope maximum ($dV/dt_{max}^{spike}$) of the segment of the EGM signal within the pre-spike search window. For example, the pre-spike search window may be defined to extend 20 ms in length prior to the local amplitude maximum $V_{max}^{spike}$. The processors analyze a slope ratio between the local slope maximum $dV/dt_{max}^{spike}$ and the global slope minimum $dV/dt_{min}$. The processors determine whether the local slope maximum $dV/dt_{max}^{spike}$ in the pre-spike search window satisfies a slope ratio condition relative to a global slope characteristic of the EGM signal. For example, the processors determine whether the local slope maximum $dV/dt_{max}^{spike}$ is greater than a predetermined factor of the global slope minimum $dV/dt_{min}$. For example, the processors may determine where the local slope maximum $dV/dt_{max}^{spike}$ within a 20 ms pre-spike search window is 30% or more of the global slope minimum $dV/dt_{min}$ (e.g., $dV/dt_{max}^{spike} < (0.3) \times (dV/dt_{min})$). It is recognized that the durations of the windows and the size of the factors may be varied.

When the slope ratio condition at 338 is satisfied, flow branches to 342. At 342, the one or more processors set a second deflection flag to a true condition. Alternatively, when the slope ratio condition at 338 is not satisfied, flow continues to 340. At 340, the one or more processors set the second deflection flag to a false condition.

Thereafter, flow moves to 344, where the one or more processors determine whether one or both of the first and second deflection flags are true. When both deflection flags are true, flow continues to 346. When one or both of the deflection flags are false, flow branches to 348. At 348, flow returns to FIG. 3A. At 346, the one or more processors adjust the QRS start time. For example, the processors may set the QRS start time at a point in time, before the local amplitude maximum $V_{max}^{spike}$ identified at 330, where a slope in the EGM signal satisfies a slope ratio relative to the local slope maximum $dV/dt_{max}^{spike}$. For example, the QRS start time may be set to a point in time where the EGM signal has a slope that approximately equals or does not exceed 30% of the local slope maximum $dV/dt_{max}^{spike}$. Thereafter, flow moves to 348 and the process returns to FIG. 3A where the QRS duration is determined as explained in connection with FIG. 3A.

Figure 4A:
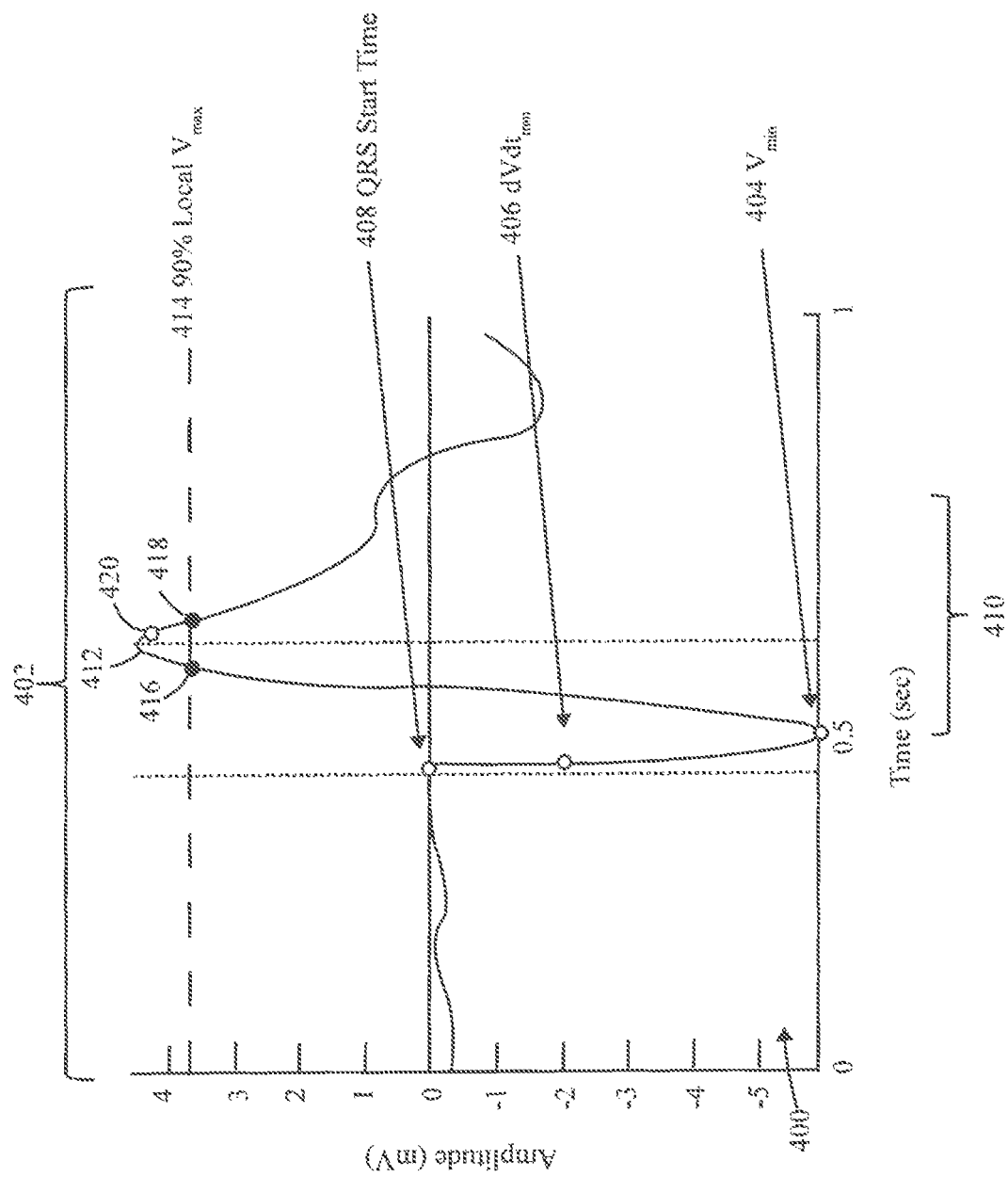
FIG. 4A illustrates an example EGM signal for one cardiac cycle along with notations for characteristics of interest analyzed in accordance with embodiments herein.

Next, the operations of FIGS. 3A-3B are described in connection with example EGM signals of FIGS. 4A and 4B. FIG. 4A illustrates an example EGM signal for one cardiac cycle along with notations for characteristics of interest analyzed in accordance with embodiments herein. In FIG. 4A, the EGM signal 400 extends over a cardiac cycle as noted by bracket 402. The EGM signal 400 for the cardiac cycle is analyzed to identify a global amplitude minimum $V_{min}$ 404 (at 304 in FIG. 3A). Thereafter, the slope of the EGM signal 400 is identified at various points along the EGM signal over the cardiac cycle. The slopes at the various points are analyzed to identify a global slope minimum in the negative direction $dV/dt_{min}$ 406. Next, the process defines the QRS start time 408. For example, the QRS start time is defined as a last point along the QRS complex before a point in time at which the global slope minimum $dV/dt_{min}$ exhibits at least one of two conditions. For example, one condition may be that a slope/derivative of the EGM signal V(t) exceeds or is approximately 5% of the negative global slope minimum $dV/dt_{min}$. The other condition may be that the EGM signal V(t) exceeds or is approximately 10% of the global amplitude minimum $V_{min}$. It is recognized that the foregoing percentages are examples and may vary. The conditions are found to be satisfied at the point denoted by 408.

Figure 3C:
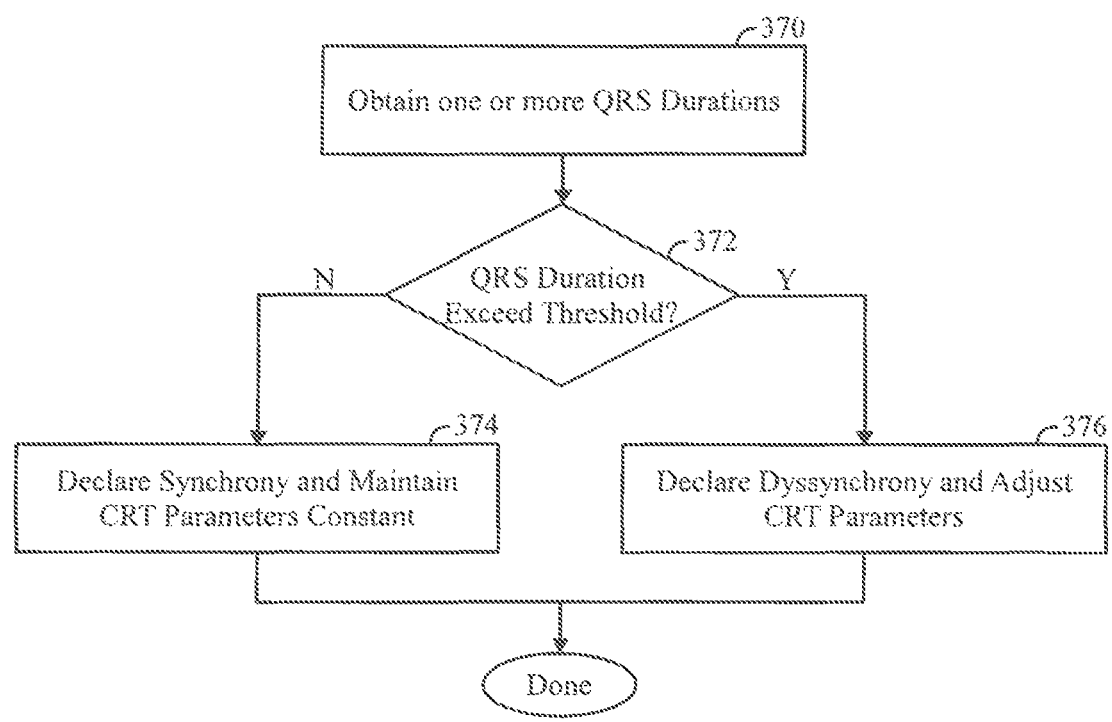
FIG. 3C illustrates a process for determining synchrony or dyssynchrony within physiologic behavior of the heart in accordance with embodiments herein.

FIG. 3C illustrates a process for determining synchrony dyssynchrony within physiologic behavior of the heart in accordance with embodiments herein. At 370, the one or more processors obtain one or more QRS durations. The QRS durations may be obtained from memory (such as when stored during a prior iteration through FIG. 3A). Additionally or alternatively, at 370, the one or more processors may implement the process of FIG. 3A to collect new EGM signals and determine one or more corresponding QRS durations.

At 372, the one or more processors compare the QRS duration to one or more QRS duration thresholds to determine whether the QRS complex has a "broad" QRS complex or "narrow" QRS complex. A broad QRS complex is a QRS complex having a QRS duration that exceeds the corresponding threshold is indicative of dyssynchrony within the physiologic behavior of the heart. Dyssynchrony may indicate that a CRT therapy is not effective. A narrow QRS complex, is a QRS complex having a QRS duration below the corresponding threshold is indicative of synchrony within the cardiac cycle. Synchrony may indicate that a CRT therapy is effective.

When the QRS duration exceeds the QRS duration threshold, flow branches three 376. When the QRS duration falls below the QRS duration threshold, flow continues to 374. At 374, the one or more processors of an IMD, external device and the like determine to maintain the CRT therapy constant. At 376, the one or more processors adjust the CRT therapy by adjusting one or more CRT parameters.

In accordance with the operations of FIG. 3C, synchrony or dyssynchrony is declared based on whether the QRS duration falls below, equals or exceeds the QRS threshold. When a QRS duration exceeds the threshold and indicates dyssynchrony in the physiologic behavior of the heart, the IMD, external device or other processors within the system may determine to change one or more CRT parameters. For example, an IMD may adjust an atrioventricular delay, an interventricular delay, a pacing rate, and/or one or more other CRT parameters in an effort to determine a CRT therapy that achieves synchrony in the physiologic behavior of the heart.

In the example of FIG. 4A, the QRS start time is not preceded by any candidate deflections spikes. More specifically, the portion of the EGM signal that precedes the QRS start time 408 exhibits only negative amplitudes and does not exceed the amplitude of the QRS start time 408. Accordingly, the optional operations of FIG. 4B are skipped.

Next, the process defines a search window 410 that follows the global amplitude minimum 404. For example, a search window 410 may be defined to have a length of 200 ms following the global amplitude minimum 404. The EGM signal segment within the search window 410 is analyzed to identify a local amplitude maximum 412. A threshold amplitude 414 is defined based on the local amplitude maximum 412. For example, the threshold amplitude 414 may be defined to equal 90% of the local amplitude maximum 412. The EGM signal segment surrounding the local amplitude maximum 412 is analyzed to identify first and second threshold crossings 416 and 418. Next, a QRS end time 420 is identified as a point along the EGM signal that is positioned a desired distance between the first and second threshold crossings 416 and 418. For example, the QRS endpoint 420 may be defined to correspond to a point along the EGM signal that is approximately 80% across the distance between the first and second threshold crossings 416 and 418. Based on the QRS start time 408 and the QRS end time 420, a QRS duration is determined.

Figure 4B:
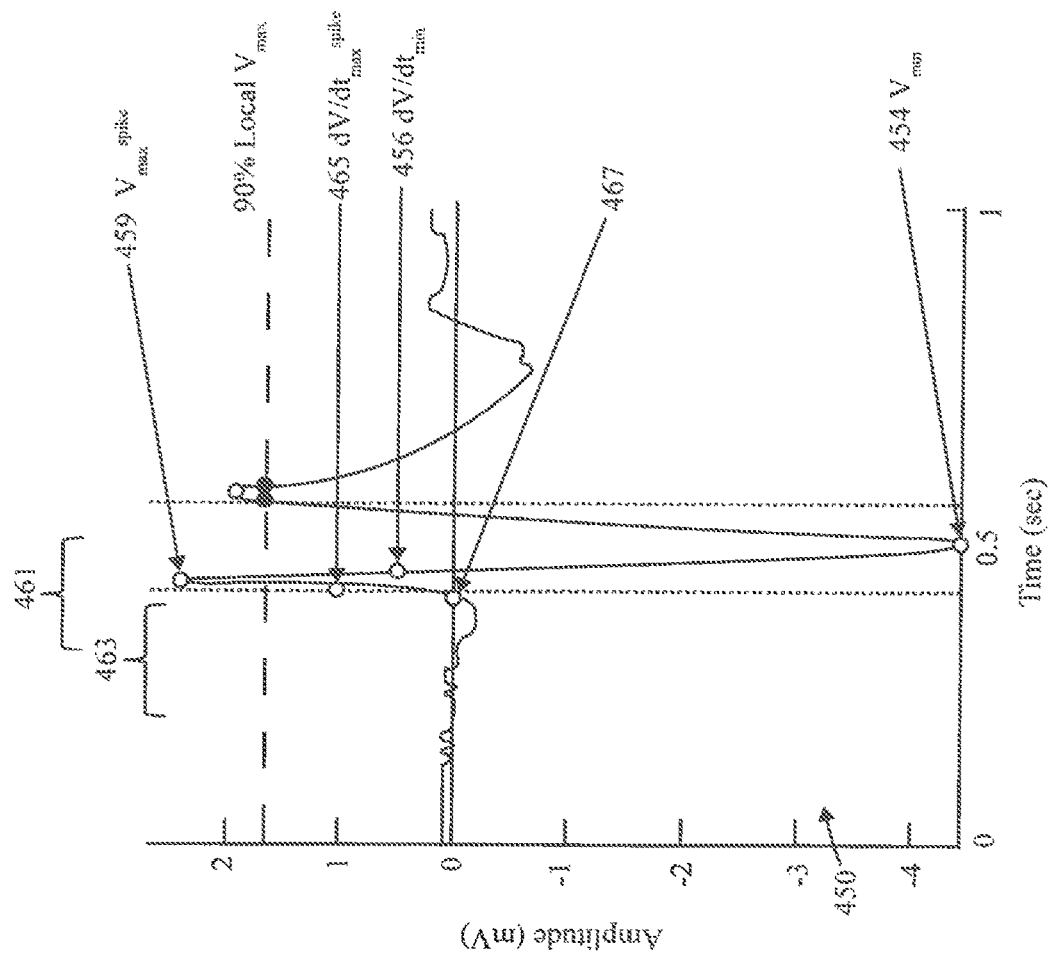
FIG. 4B illustrates an example EGM signal for one cardiac cycle along with notations for characteristics of interest analyzed in accordance with embodiments herein.

FIG. 4B illustrates an example EGM signal for one cardiac cycle along with notations for characteristics of interest analyzed in accordance with embodiments herein. The EGM signal 450 is analyzed to identify a global amplitude minimum $V_{min}$ 454. The slopes at the various points are analyzed to identify a global slope minimum in the negative direction $dV/dt_{min}$ 456. Next, the process defines an initial QRS start time. However, the EGM signal includes a deflection peak 459 that exist prior to the initial QRS start time, and thus the process of FIG. 3B is implemented to test for a potential candidate deflection spike.

In connection with the process of FIG. 3B, a search window 461 is defined proximate to an initial QRS start time. The EGM signal within the search window 461 is analyzed to identify a local amplitude maximum 459 ($V_{max}^{spike}$). The EGM signal within the search window 461 is further analyzed for the two conditions of interest. One condition is whether the EGM signal is monotonically increasing or decreasing over the search window 461. In the example of FIG. 4B, the EGM signal is not monotonically increasing or decreasing, but instead includes a local maximum at 459. As the second condition, the process analyzes a pre-spike search window 463 that precedes the local amplitude maximum 459. A local slope maximum 465 ($dV/dt_{max}^{spike}$) is identified from the EGM segment within the pre-spike search window 463. Based thereon, the QRS start time 467 is identified as the point along the EGM signal where the slope satisfies a slope ratio. For example, the process determines a point along the EGM signal where the slope is 30% or more of the global slope minimum 456 ($dV/dt_{min}$).

External Device

Figure 5:
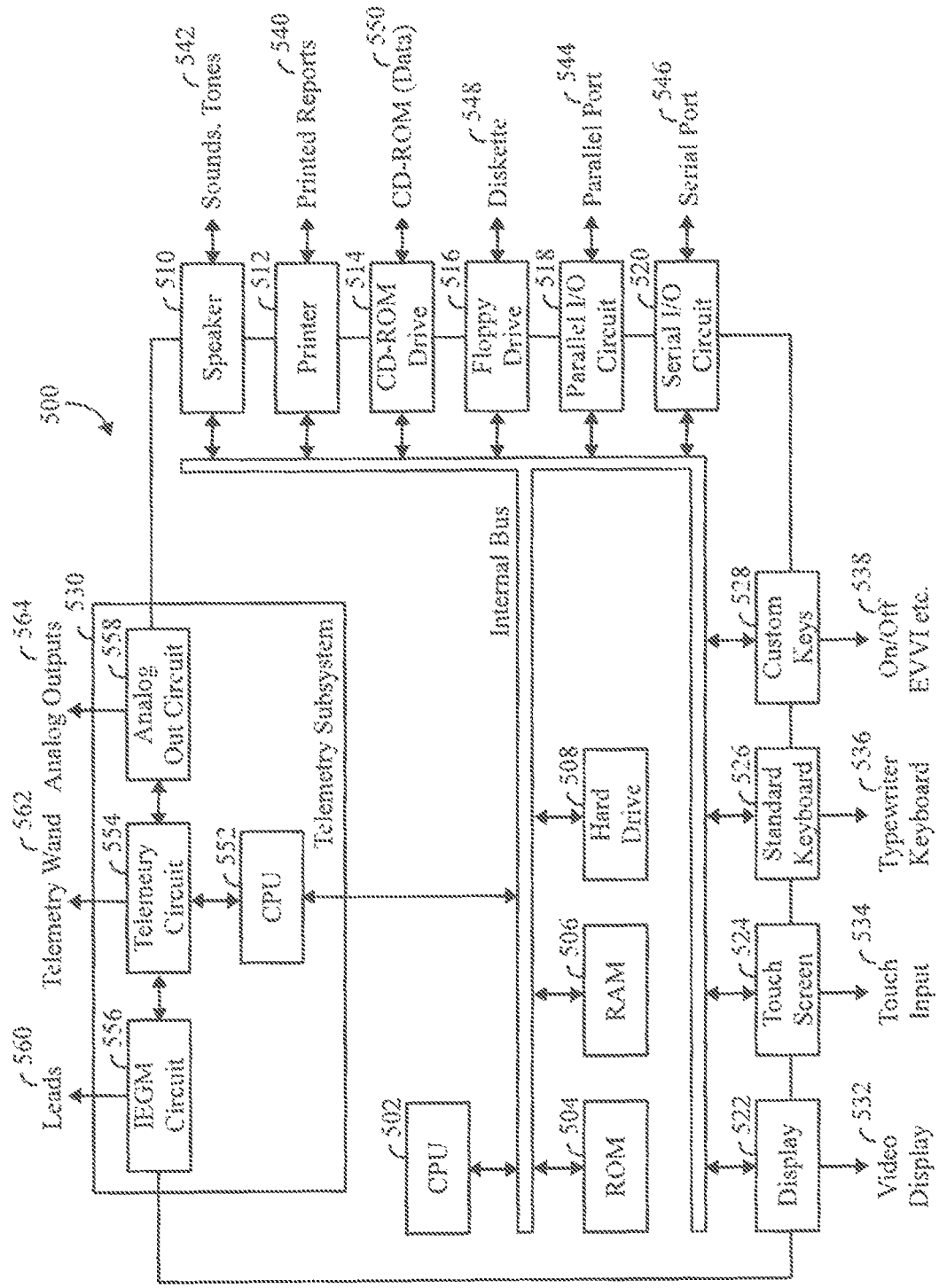
FIG. 5 illustrates a functional block diagram of the external device that is operated in accordance with the processes described herein and to interface with implantable medical devices as described herein.

FIG. 5 illustrates a functional block diagram of the external device 500 that is operated in accordance with the processes described herein and to interface with implantable medical devices as described herein. The external device 500 may be a workstation, a portable computer, an IMD programmer, a PDA, a cell phone and the like. The external device 500 includes an internal bus that connects/interfaces with a Central Processing Unit (CPU) 502, ROM 504, RAM 506, a hard drive 508, the speaker 510, a printer 512, a CD-ROM drive 514, a floppy drive 516, a parallel I/O circuit 518, a serial I/O circuit 520, the display 522, a touch screen 524, a standard keyboard connection 526, custom keys 528, and a telemetry subsystem 530. The internal has is an address/data bus that transfers information between the various components described herein. The hard drive 508 may store operational programs as well as data, such as waveform templates and detection thresholds.

The CPU 502 typically includes a microprocessor, a micro-controller, or equivalent control circuitry, designed specifically to control interfacing with the external device 500 and with the IMD 100. The CPU 502 performs the QRS duration estimation process discussed above. The CPU 502 may include RAM or ROM memory, logic and timing circuitry, condition machine circuitry, and I/O circuitry to interface with the IMD 100. The display 522 (e.g., may be connected to the video display 532). The touch screen 524 may display graphic information relating to the IMD 100. The display 522 displays various information related to the processes described herein. The touch screen 524 accepts a user's touch input 534 when selections are made. The keyboard 526 (e.g., a typewriter keyboard 536) allows the user to enter data to the displayed fields, as well as interface with the telemetry subsystem 530. Furthermore, custom keys 528 turn on/off 538 (e.g., EVVI) the external device 500. The printer 512 prints copies of reports 540 for a physician to review or to be placed in a patient file, and speaker 510 provides an audible warning (e.g., sounds and tones 542) to the user. The parallel I/O circuit 518 interfaces with a parallel port 544. The serial I/O circuit 520 interfaces with a serial port 546. The floppy drive 516 accepts diskettes 548. Optionally, the floppy drive 516 may include a USB port or other interface capable of communicating with a USB device such as a memory stick. The CD-ROM drive 514 accepts CD ROMs 550.

The telemetry subsystem 530 includes a central processing unit (CPU) 552 in electrical communication with a telemetry circuit 554, which communicates with both an EGM circuit 556 and an analog out circuit 558. The circuit 556 may be connected to leads 560. The circuit 556 is also connected to the implantable leads 114, 116 and 118 to receive and process EGM cardiac signals as discussed above. Optionally, the EGM cardiac signals sensed by the leads 114, 116 and 118 may be collected by the IMD 100 and then transmitted wirelessly to the telemetry subsystem 530 input.

The telemetry circuit 554 is connected to a telemetry wand 562. The analog out circuit 558 includes communication circuits to communicate with analog outputs 564. The external device 500 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 500 to the IMD 100.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method, comprising:
   under control of one or more processors within an implantable medical device (IMD);
   collecting an intra-cardiac electrogram (EGM) signal associated with an event of interest;
   determining a global amplitude characteristic (GAC) and a global slope characteristic (GSC) from the EGM signal;
   defining a QRS start time, within the EGM signal, based on the GSC;
   determining a local amplitude characteristic (LAC) for a segment of the EGM signal within a search window that is positioned based on the GAC;
   defining a QRS end time, within the EGM signal, based on the LAC; and
   calculating a QRS duration based on the QRS start time and QRS end time.

2. The method of claim 1, wherein the GAC represents a global amplitude minimum experienced by the EGM signal over the event of interest.

3. The method of claim 2, wherein the GSC represents a global slope minimum experienced by the EGM signal over the event of interest.

4. The method of claim 3, wherein the defining the QRS start time further comprises defining the QRS start time as a last time point along the QRS complex before a point in time at which the GSC exhibited at least one of: I) a derivative of the EGM signal exceeds the global slope characteristic by a predetermined slope factor or II) the EGM signal exceeds the global amplitude minimum by a predetermined amplitude factor.

5. The method of claim 1, wherein the determining the GSC includes calculating derivatives at points along the EGM signal over a search window that precedes the GAC and determining the global slope minimum in a negative direction based on the derivatives.

6. The method of claim 1, further comprising reducing the QRS start time by an amount corresponding to an isoelectric drop.

7. The method of claim 1, wherein the determining the LAC comprises determining a local amplitude maximum that occurs within a search window after the GAC; and identifying threshold crossings of the EGM signal that surround the local amplitude maximum, the threshold crossings representing points at which the EGM signal cross a threshold amplitude that is defined based on the local amplitude maximum.

8. The method of claim 7, wherein the QRS end time is determined to correspond to a point in time along the EGM signal at a set point between the threshold crossings.

9. The method of claim 1, further comprising determining whether a deflection spike occurs prior to the QRS start time, verifying whether the deflection spike represents a local maximum amplitude, and adjusting the QRS start time based on the verifying to a point in time before the deflection spike.

10. The method of claim 1, further comprising determining whether a deflection spike occurs prior to the QRS start time, verifying whether a slope of the EGM signal within a search window prior to the deflection spike falls below the global slope characteristic by a slope factor, and adjusting the QRS start time based on the verifying to a point in time before the deflection spike.

11. The method of claim 1, further comprising automatically programming at least one parameter for a synchronous atrial and ventricular cardiac resynchronization therapy based on the QRS duration.

12. A system comprising:
   an implantable lead having electrodes configured to be located proximate to a heart, the electrodes defining a sensing vector through a region of interest in the heart;
   memory to store program instructions; and a processor that, when executing the program instructions, is configured to:

collect an intra-cardiac electrogram (EGM) signal along the sensing vector, the EGM signal associated with an event of interest;

determine a global amplitude characteristic (GAC) and a global slope characteristic (GSC) from the EGM signal;

define a QRS start time, within the EGM signal, based on the GSC;

determine a local amplitude characteristic (LAC) for a segment of the EGM signal within a search window that is positioned based on the GAC;

define a QRS end time, within the EGM signal, based on the LAC; and calculate a QRS duration based on the QRS start time and QRS end time.

13. The system of claim 12, wherein the GAC represents a global amplitude minimum experienced by the EGM signal over the event of interest.

14. The system of claim 12, wherein the GSC represents a global slope minimum experienced by the EGM signal over the event of interest.

15. The system of claim 12, wherein the processor is configured to define the QRS start time as a last time point along the QRS complex before a point in time at which the GSC exhibited at least one of: I) a slope of the EGM signal exceeds the global slope minimum by a predetermined slope factor or II) the EGM signal exceeds the global amplitude minimum by a predetermined amplitude factor.

16. The system of claim 12, wherein the processor is configured to calculate derivatives at points along the EGM signal over a search window that precedes the GAC and to determine the global slope minimum in a negative direction based on the derivatives.

17. The system of claim 12, further comprising reducing the QRS start time by an amount corresponding to an isoelectric drop.

18. The system of claim 12, wherein the determining the LAC comprises determining a local amplitude maximum that occurs within a time window after the GAC; and identifying threshold crossings of the EGM signal that surround the local amplitude maximum, the threshold crossings representing points at which the EGM signal cross a threshold amplitude that is defined based on the local amplitude maximum.

19. The system of claim 12, wherein the QRS end time is determined to correspond to a point in time along the EGM signal at a set point between the threshold crossings.

20. The system of claim 12, wherein the processor is further configured to determine whether a deflection spike occurs prior to the QRS start time, verifying whether the deflection spike represents a local maximum amplitude, and adjusting the QRS start time based on the verifying to a point in time before the deflection spike.

21. The system of claim 12, wherein the processor is further configured to determine whether a deflection spike occurs prior to the QRS start time, verifying whether a slope of the EGM signal within a time window prior to the deflection spike falls below the global slope characteristic by a slope factor, and, based on the verifying, adjusting the QRS start time to a point in time before the deflection spike.

22. The system of claim 12, wherein the processor is further configured to automatically program at least one parameter for a synchronous atrial and ventricular cardiac resynchronization therapy based on the QRS duration.

* * * * *